US00PP22653P2

(12) United States Plant Patent
Burton

(10) Patent No.: US PP22,653 P2
(45) Date of Patent: Apr. 17, 2012

(54) ***HEBE* PLANT NAMED 'GRACE KELLY'**

(50) Latin Name: ***Hebe* hybrid**
Varietal Denomination: Grace Kelly

(76) Inventor: Stephen Burton, Cambridge (NZ)

( * ) Notice: Subject to any disclaimer, the term of this patent is extended or adjusted under 35 U.S.C. 154(b) by 0 days.

(21) Appl. No.: 13/065,116

(22) Filed: Mar. 15, 2011

(51) Int. Cl.
*A01H 5/00* (2006.01)

(52) U.S. Cl. ..... Plt./251; Plt./225
(58) Field of Classification Search ..... Plt./251, Plt./226, 263.1
See application file for complete search history.

*Primary Examiner* — Kent L Bell
(74) *Attorney, Agent, or Firm* — Penny J. Aguirre

(57) ABSTRACT

A new cultivar of *Hebe*, 'Grace Kelly', characterized by its large leaves that are variegated with greyed-green centers and distinct creamy white margins with a red-purple central vein, its young leaves that are tinged with yellow at the tips, its foliage that is resistant to leaf spot and its medium sized racemes that are red-purple in color.

2 Drawing Sheets

Botanical classification: *Hebe* hybrid.
Cultivar designation: 'Grace Kelly'.

BACKGROUND OF THE INVENTION

The present invention relates to a new and distinct cultivar of *Hebe*, botanically of hybrid origin and in the group Comm. Ex. Juss. and known as *Hebe* 'Grace Kelly' and will be referred to hereafter by its cultivar name, 'Grace Kelly'. 'Grace Kelly' is grown for use as a container plant and as a landscape shrub.

The new cultivar was discovered as a unique chance seedling in the Inventor's nursery in summer of 2007 in Cambridge, New Zealand. The parentage is unknown as the new cultivar resulted from open pollination in a trial plot planted with a collection of *Hebe* grown from seed.

Asexual reproduction of the new cultivar was first accomplished by the Inventor using terminal stem cuttings in Cambridge, New Zealand in 2007. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Grace Kelly' as a new and distinct cultivar of *Hebe*.

1. 'Grace Kelly' exhibits large leaves, reaching up to 9 cm in length and 3 cm in width.
2. 'Grace Kelly' exhibits foliage that is variegated with greyed-green centers and distinct creamy white margins and a red-purple central vein.
3. 'Grace Kelly' exhibits foliage that is resistant to leaf spot.
4. 'Grace Kelly' exhibits young leaves that are tinged with yellow at the tips.
5. 'Grace Kelly' exhibits medium sized racemes that are red-purple in color.

'Grace Kelly' was observed to be unique from all of the unnamed plants in the collection from which it was derived in having clearer defined leaf variegation, larger leaves, and in having a greater resistance to leaf spot. 'Grace Kelly' can be most closely compared to the cultivars 'Waireka' and 'Orphan Annie' (both un-patented). 'Waireka' differs from 'Grace Kelly' in having variegated foliage that is green with whiter margins, in having smaller leaves, and in flowers that are lighter in color and mauve-purple rather than red-purple. 'Orphan Annie' differs from 'Grace Kelly' in having variegated foliage that is green with yellow margins, in having new leaf tips that are tinged with magenta rather than yellow, in having smaller leaves, and in having flowers that are more cerise pink in color.

BRIEF DESCRIPTION OF THE DRAWING

The accompanying colored photographs illustrate the overall appearance and distinct characteristics of the new *Hebe*. The photographs were taken of a plant approximately one year in age as grown in an 18-cm container outdoors in Cambridge, New Zealand.

The photograph in FIG. 1 is a side view of 'Grace Kelly' in bloom.

Figure 1:
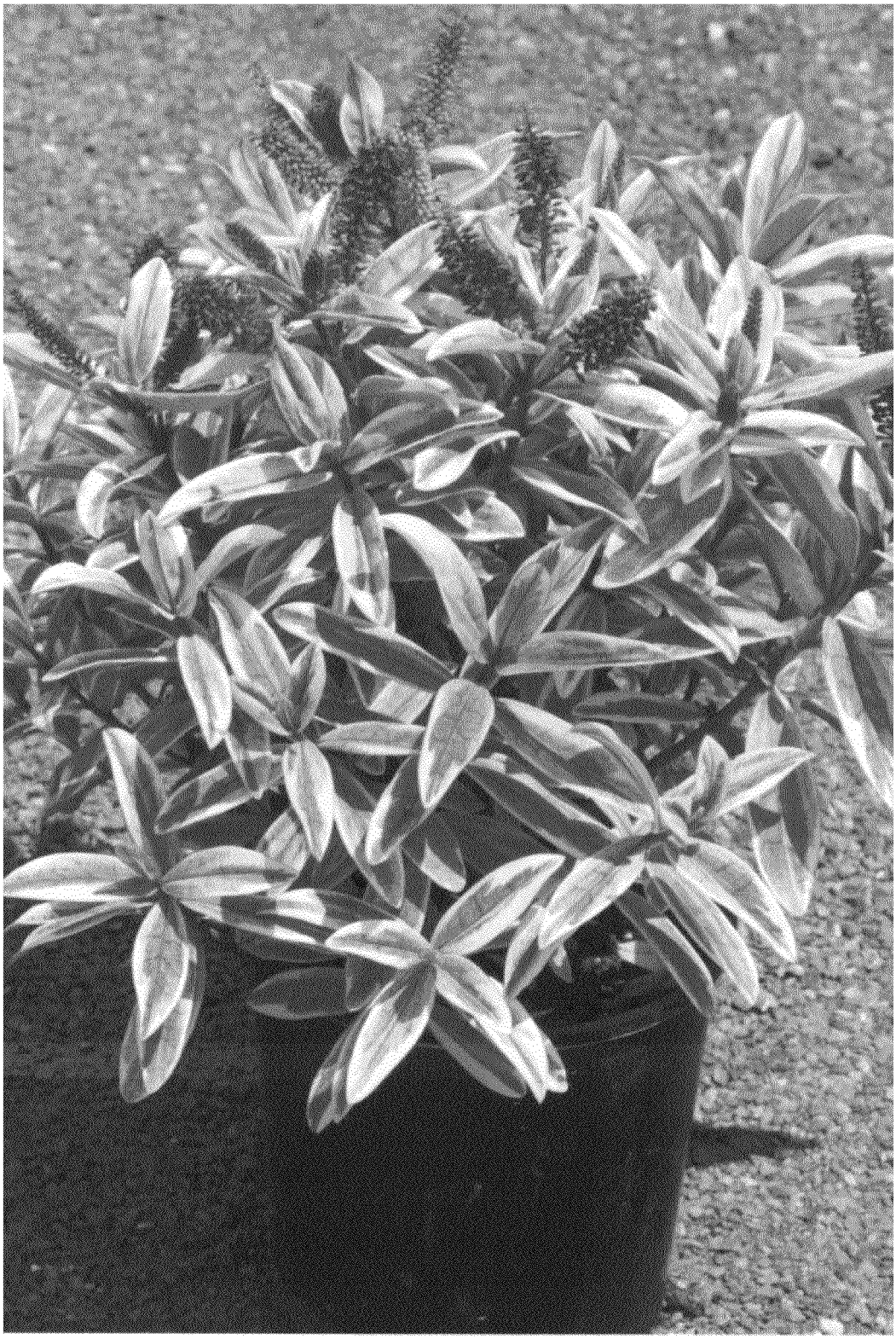
Figure 2:
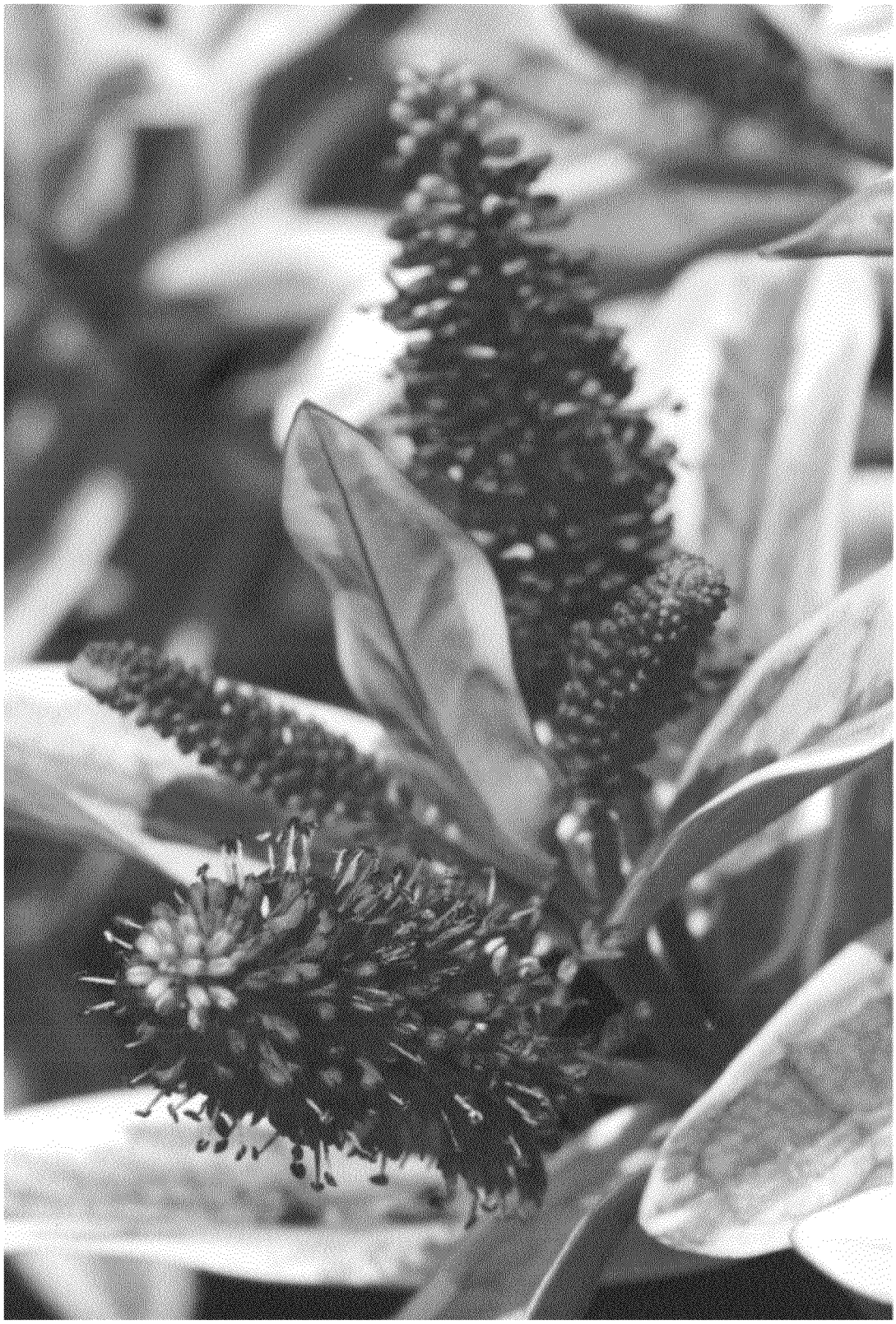

The photograph in FIG. 2 provides a close-up view of the inflorescences and leaves of 'Grace Kelly'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of one year-old plants of the new cultivar as grown outdoors in 18-cm containers in Cambridge, New Zealand. Plants were grown under average day temperatures of 20° to 28° C. and average night temperatures of 12° to 16° C. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General plant characteristics:

*Plant type*.—Perennial shrub.

*Plant habit*.—Rounded, upright and spreading.

*Flowering period*.—12 weeks in mid to late summer in New Zealand.

*Height and spread*.—Reaches 60 to 80 cm in height and about 80 cm in width.

*Hardiness*.—U.S.D.A. Zones 9b, 10a, and 10b.

*Disease resistance*.—Resistant to leaf spot.

*Root description*.—Fibrous and fine, 1 to 3 mm in diameter, 176D in color.

Growth and propagation:

*Growth rate*.—Vigorous.

*Propagation type*.—Terminal stem cuttings.

*Root initiation*.—About 10 days at 20° C. under mist in a greenhouse and ambient light.

*Root development*.—7 weeks from rooted cutting to liner transfer and about 12 weeks to fully develop a liner with one trim.

Stem description:

*Stem size*.—Lateral branches are an average of 30 to 50 cm in length and 4 to 6 mm in width.

*Stem shape*.—Round.

*Stem color*.—N77C.

*Stem surface*.—Smooth.

*Stem Strength*.—Brittle.

*Internode length*.—Average of 7 mm.

*Branching habit*.—Freely branched from base, average of 10 lateral branches.

Foliage description:

*Leaf shape*.—Oblong.

*Leaf division*.—Single.

*Leaf base*.—Rounded.

*Leaf apex*.—Broadly acute with small mucronate tip.

*Leaf venation*.—Only mid rib is visible, 71A in color on upper and lower surface.

*Leaf margins*.—Smooth entire.

*Leaf attachment*.—Sessile.

*Leaf arrangement*.—Opposite simple sessile.

*Leaf surface*.—Glabrous.

*Leaf color*.—Upper young surface; margins 11C and centers a blend of 194A and 137B, mature upper surface; margins 11D and centers a blend of 194A to 194B and 137B, lower young surface; margins 11C and centers a blend of 194A and 137B and tinged with N77C, mature lower surface; margins 11C and centers 195A.

*Leaf number*.—Average of 20 to 30 per lateral branch.

*Leaf size*.—7 to 9 cm in length and 2 to 3 cm in width.

*Leaf aspect*.—Held nearly horizontal to slightly upright to stem.

*Leaf fragrance*.—None.

Flower description:

*Inflorescence type*.—Multiple florets on a raceme.

*Inflorescence size*.—5 to 6 cm in length and 1.5 to 2.5 cm in width.

*Inflorescence lastingness*.—About 4 to 6 weeks, persistant.

*Flower shape*.—Raceme is tapered with trumpet shaped florets.

*Flower fragrance*.—None.

*Flower quantity*.—Average of 60 to 70 florets per inflorescence.

*Flower arrangement*.—Paired racemes on extended peduncle from the leaf axis, 2 to 4 racemes per lateral stem.

*Flower aspect*.—Slightly drooping racemes.

*Flower size*.—Average of 8 mm in depth and 6 mm in diameter.

*Peduncles*.—Medium strength, 1 to 2 cm in length and about 1 mm in width, 187A in color, surface is sparsely covered in short hairs, round in shape, held at about a 30° angle to stem.

*Pedicels*.—Average of 2 mm in length and 1 mm in width, held at about a 50° to 60° angle to peduncle, 77A in color, surface is smooth.

*Flower buds*.—Oblong in shape and slightly pointed at the tip, 1 to 2 mm in length and 0.5 to 1 mm in diameter, 77A in color.

*Calyx*.—Cup-shaped, average of 1.5 mm in length and 2 mm in width.

*Sepals*.—3, very small and lanceolate in shape, apex is pointed, base tapers to pedicel, color of young upper and lower surface when opening; 77A, color of mature upper and lower surface; 77B, average of 1.5 mm in length and 1 mm in width.

*Corolla*.—3 to 4 petals form a ring to comprise trumpet shape.

*Petals*.—From 3 to 4, about 3 to 4 mm in length and 1 to 2 mm in width, smooth margins, apex rounded, upper and lower surface is glabrous, color of upper and lower surface when opening; 81A, color of upper surface when fully open; 83A, color of lower surface when fully open; 83C with fused base, color of both surfaces after fading; 83D.

Reproductive organs:

*Gynoecium*.—1 Pistil, 8 to 9 mm in length, stigma is slightly rounded in shape and 187A in color, style is about 6 to 7 mm in length and 186C in color, ovary is 186C in color.

*Androcoecium*.—2 stamens, anthers are heart shaped and 200A in color, filaments are about 8 mm in length and 186C in color, pollen is moderate in quantity and 18B in color.

*Fruit and seed*.—Seed production has not been observed.

It is claimed:

1. A new and distinct cultivar of *Hebe* plant named 'Grace Kelly' as herein illustrated and described.

* * * * *